United States Patent [19]
Gilling

[11] Patent Number: 6,126,601
[45] Date of Patent: Oct. 3, 2000

[54] METHOD AND APPARATUS FOR ULTRASOUND IMAGING IN MULTIPLE MODES USING PROGRAMMABLE SIGNAL PROCESSOR

[76] Inventor: Christopher J. Gilling, 266 Parkview Ct., Pewaukee, Wis. 53072

[21] Appl. No.: 09/182,150

[22] Filed: Oct. 29, 1998

[51] Int. Cl.[7] ..................................................... A61B 8/00
[52] U.S. Cl. ........................................ 600/440; 600/443
[58] Field of Search .................................. 600/440, 443, 600/447; 73/620

[56] References Cited

U.S. PATENT DOCUMENTS

| | | | |
|---|---|---|---|
| 4,271,842 | 6/1981 | Specht et al. | 600/447 |
| 5,520,187 | 5/1996 | Snyder | 600/447 |
| 5,899,863 | 5/1999 | Hatfield et al. | 600/443 |

Primary Examiner—Marvin M. Lateef
Assistant Examiner—Ali M. Imam
Attorney, Agent, or Firm—Dennis M. Flaherty; Christian G. Cabou; Phyllis Y. Price

[57] ABSTRACT

A method for configuring an ultrasound imaging system having a programmable signal processor and an operator interface. Application codes for programming the signal processor to process signals in accordance with respective imaging modes are stored in memory. A user operates an operator interface to select one of the plurality of imaging modes. The master controller programs the signal processor with the application code corresponding to the selected imaging mode. The signal processor is programmable to process signals in the B mode, M mode, color flow imaging mode and Doppler imaging mode. Preferably, the programmable signal processor is an array of digital signal processor chips. Incoming vector data is partitioned amongst the respective digital signal processor chips. The processed vector segments are then recombined to form a vector of image data for display.

25 Claims, 7 Drawing Sheets

METHOD AND APPARATUS FOR ULTRASOUND IMAGING IN MULTIPLE MODES USING PROGRAMMABLE SIGNAL PROCESSOR

FIELD OF THE INVENTION

This invention generally relates to ultrasound imaging systems having multiple imaging modes. In particular, the invention relates to medical diagnostic imaging systems having the capability to process acoustic signals in multiple imaging modes.

BACKGROUND OF THE INVENTION

Premium medical diagnostic ultrasound imaging systems require a comprehensive set of imaging modes. These are the major imaging modes used in clinical diagnosis and include timeline Doppler, color flow Doppler, B mode and M mode. In the B mode, such ultrasound imaging systems create two-dimensional images of tissue in which the brightness of a pixel is based on the intensity of the echo return. Alternatively, in a color flow imaging mode, the movement of fluid (e.g., blood) or tissue can be imaged. Measurement of blood flow in the heart and vessels using the Doppler effect is well known. The phase shift of backscattered ultrasound waves may be used to measure the velocity of the backscatterers from tissue or blood. The Doppler shift may be displayed using different colors to represent speed and direction of flow. In the timeline Doppler imaging mode, the power spectrum of these Doppler frequency shifts are computed for visual display as velocity-time waveforms. These imaging modes are differentiated in the "midprocessor" section of the ultrasound machine. This is the machine electronics subsection located after the front-end beamformer, yet before the back-end scan conversion. Typically these midprocessor functions are implemented in separate serially pipelined semi-customized silicon chip sets and often on separate circuit boards. One such implementation is semi-configurable by the host software. Function coefficients can be configured by software, but the flow or architecture is fixed.

Across the midprocessor major imaging modes, the image data processing is highly irregular and dissimilar. The function types, ordering and flow of data are unique for each of the modes. The modes share a few common functions, such as filters, with all digital signal processing applications, but even these filters have differences. The major mode differences are significant enough to require either dedicated separate application specific hardware (as in conventional systems) or highly reconfigurable hardware. The reconfigurable hardware must be of a type which will context switch between modes at the rate matching the arriving data changes for these modes or within a few microseconds.

SUMMARY OF THE INVENTION

The present invention is an ultrasound imaging midprocessor design based on the use of a single fast general-purpose processor or an array of fast general-purpose processors to implement all major mode functions within the same silicon chips. The preferred embodiment utilizes very fast inexpensive general-purpose digital signal processors (DSPs). Thus, instead of separate dedicated silicon chips implementing each major mode's functions, a common silicon chip set implements all modes. Alternatively, the array of processors can be replaced with a single processor having sufficient processing power. Many multi-DSP array architecture arrangements are possible, including serial, full parallel, mesh, piped, hypercube, tree and irregular (matching a particular function flow).

In accordance with the invention, all major mode image data arrives from the front end at the sample rate, down range and in vector format with numerous vectors concatenated in time. An input block for the multi-DSP array collects this image data and the vector rate configuration data, optionally decimates the data, and parses the data amongst the DSP blocks. The data parsing can be a mix of down range and across vector spatial positions. After gathering this data and receiving the frame and vector rate configuration data, the DSP blocks process this data to meet the active major mode's functional needs. After the completion of the signal processing task, the DSP blocks send their data segments to an output block, which recombines the data segments and sends the recombined data to the back end, i.e., the scan converter.

The general-purpose DSP solution in accordance with the invention has important advantages over a large customized ASIC solution. The functionality of the DSP is implemented in software, which provides for a greater change flexibility and more rapid improvements. This is of high value in an area of the system most often affected by image quality improvements. The software solution also lowers upgrade costs by eliminating the need for replacement hardware.

The general-purpose DSP solution offers much lower product costs than conventional designs. In particular, the general-purpose DSP solution employs the same silicon chips for all modes rather than having most of the silicon chips inactive during any one models data processing. This is enabled by the fast context switch time and function flexibility of the highly reconfigurable general-purpose DSP solution, as well as by the single-mode beamforming which is typical of conventional ultrasound imaging systems. At any given time, either a B-mode, M-mode, color flow or Doppler vector is being beamformed. A single set of flexible silicon chips processes all modes, thus keeping the silicon processing elements functioning at a relatively higher level. This high silicon utilization level creates a low-cost alternative similar to a large customized ASIC implementation. This solution is also more scaleable for performance and cost. Different populations of DSP blocks can be used to support variations in tiers of system requirements and product performance/cost levels. Little to no hardware or software design change is required to support this scaleability.

DETAILED DESCRIPTION OF THE PREFERRED EMBODIMENTS

Figure 1:
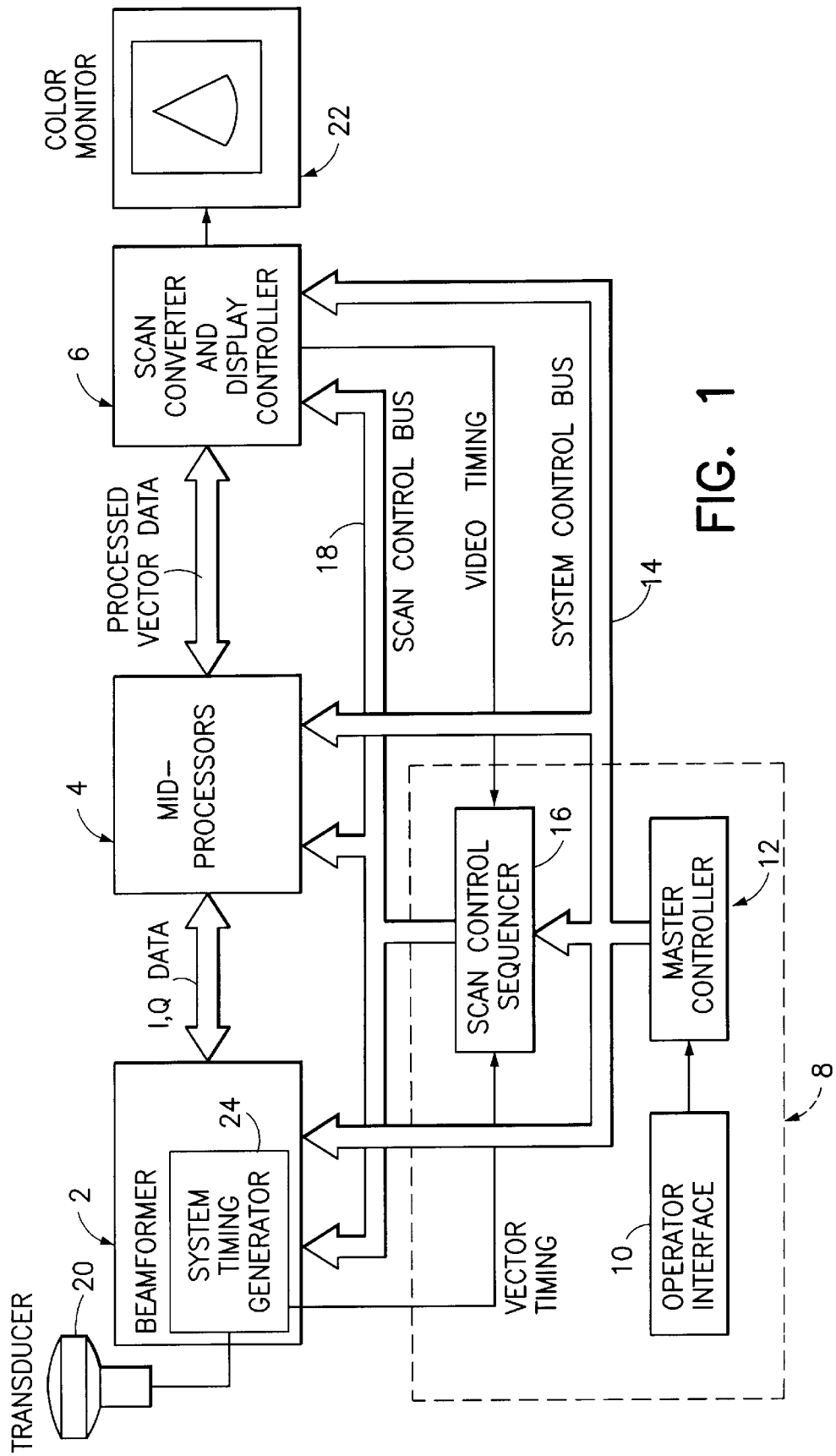
FIG. 1 is a block diagram showing the major functional blocks of a conventional real-time ultrasound imaging system.

One conventional ultrasound imaging system, generally depicted in FIG. 1, comprises four main subsystems: a beamformer 2, a midprocessor subsystem 4 (including a separate midprocessor for each different mode), a scan converter/display controller subsystem 6 and a kernel 8. System control is centered in the kernel 8, which accepts operator inputs through an operator interface 10 and in turn controls the various subsystems. The master controller 12 performs system level control functions. It accepts inputs from the operator via the operator interface 10 as well as system status changes (e.g., mode changes) and makes appropriate system changes either directly or via the scan controller. The system control bus 14 provides the interface from the master controller to the subsystems. The scan control sequencer 16 provides real-time (acoustic vector rate) control inputs to the beamformer 2, to the system timing generator 24 and to subsystems 4 and 6. The scan control sequencer 16 is programmed by the master controller with the vector sequences and synchronization options for acoustic frame acquisitions. Thus, the scan control sequencer 16 controls the beam distribution and the beam density. The scan control sequencer 16 transmits the beam parameters defined by the master controller to the subsystems via scan control bus 18.

The main data path begins with the analog RF inputs to the beamformer board 2 from the transducer 20. The beamformer board 2 is responsible for the transmit and receive beamforming. The beamformer's signal inputs are the low-level analog RF signals from the transducer elements. The beamformer board 2, which comprises a beamformer and a demodulator, outputs two summed digital baseband I and Q receive beams formed from spliced data samples. These data samples are in turn derived from the reflected ultrasound from respective focal zones of the transmitted beams. The I and Q data is sent to the equalization board 3, which incorporates a bandpass filter and time-gain control. The filter is an FIR filter programmed with a set of filter coefficients to pass a band of frequencies centered at the fundamental frequency $f_0$ of the transmit waveform or a (sub)harmonic frequency thereof.

The image data output from the equalization board 3 is sent to the midprocessor subsystem 4, where it is processed according to the acquisition mode and output as processed vector data to the scan converter/display controller subsystem 6. Subsystem 6 accepts the processed vector data, interpolates where necessary, and outputs the video display signals for the image to a color monitor 22. The displayed image is a sector scan representing the tissue and/or blood flow in a plane through the body being imaged.

Figure 2:
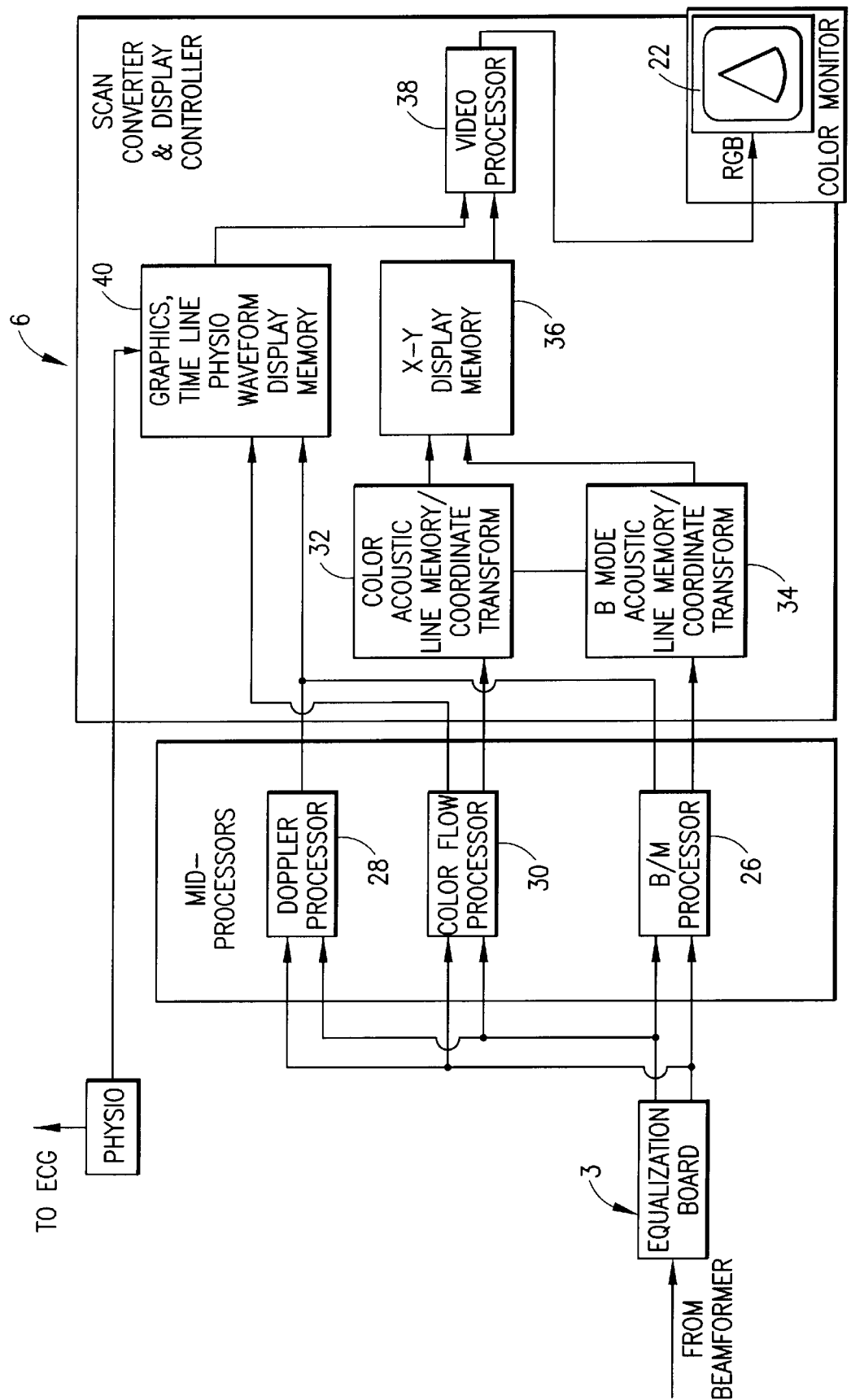
FIG. 2 is a block diagram showing the components of the midprocessor and scan converter/display controller subsystems of the system depicted in FIG. 1.

FIG. 2 shows the midprocessor and scan converter subsystems in more detail. The B/M midprocessor 26 converts the baseband I and Q data from the equalization board 3 into a log-compressed version of the signal envelope. The B-mode function images the time-varying amplitude of the envelope of the signal as a gray scale. The envelope of a baseband signal is the magnitude of the vector which I and Q represent. The I,Q phase angle is not used in the B/M display. The magnitude of the signal is the square root of the sum of the squares of the orthogonal components, i.e., $(I^2+Q^2)^{1/2}$.

The color flow processor 30 is used to provide a real-time two-dimensional image of blood velocity in the imaging plane. The frequency of sound waves reflecting from the inside of blood vessels, heart cavities, etc. is shifted in proportion to the velocity of the blood cells: positively shifted for cells moving towards the transducer and negatively for those moving away. The blood velocity is calculated by measuring the phase shift from firing to firing at a specific range gate. Instead of measuring the Doppler spectrum at one range gate in the image, mean blood velocity from multiple vector positions and multiple range gates along each vector are calculated, and a two-dimensional image is made from this information. The color flow processor 30 receives the summed left and right, complex I/Q data from the equalization board 3 and processes it to calculate the mean blood velocity, variance (representing blood turbulence) and total prenormalization power for all sample volumes within an operator-defined region.

One of the primary advantages of Doppler ultrasound is that it can provide noninvasive and quantitative measurements of blood flow in vessels. Given the angle θ between the insonifying beam and the flow axis, the magnitude of the velocity vector can be determined by the standard Doppler equation:

$$v=cf_d/(2f_0 \cos \theta)$$

where c is the speed of sound in blood, $f_0$ is the transmit frequency and $f_d$ is the motion-induced Doppler frequency shift in the backscattered ultra-sound signal.

The color and B-mode acoustic line memories 32 and 34 respectively accept processed digital data from the color flow and B-mode midprocessors. These components of the scan converter also perform the coordinate transformation of the color flow and B-mode data from polar coordinate (R-θ) sector format or Cartesian coordinate linear format to appropriately scaled Cartesian coordinate display pixel data, which is stored in the X-Y display memory 36. The M mode and Doppler data types as well as graphics and physio data are stored in display memory 40. The video processor 38, which is connected to both display memories 36 and 40, multiplexes between the graphics/physio data, image data and reference bar data to display the resulting image in a raster scan format on video monitor 22. Additionally it provides for various gray-scale and color maps as well as combining the gray-scale and color images.

In spectral Doppler imaging, the I/Q components are integrated (summed) over a specific time interval and then sampled by the Doppler midprocessor 28. The summing interval and transmit burst length together define the length of the sample volume as specified by the user. A "sum and dump" operation effectively yields the Doppler signal backscattered from the sample volume. The Doppler signal is passed through a wall filter which rejects any clutter in the signal corresponding to stationary or very slow moving tissue. The filtered output is then fed into a spectrum analyzer, which typically takes Fast Fourier Transforms (FFTS) over a moving time window of 64 to 128 samples. Each FFT power spectrum is compressed and then output by the Doppler midprocessor 28 to time-line display memory 40. The video processor 38 maps the compressed Doppler data to a grey scale for display on the monitor 22 as a single spectral line at a particular time point in the Doppler velocity (frequency) versus time spectrogram.

Figure 3:
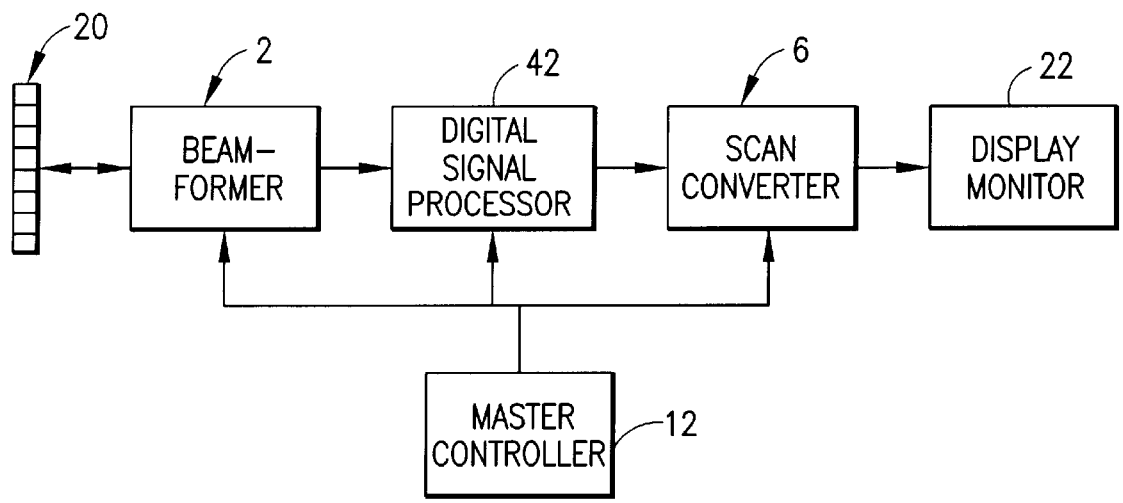
FIG. 3 is a block diagram showing an ultrasound imaging system in accordance with the invention.

In accordance with the broad concept of the invention, the three midprocessors 26, 28 and 30 shown in FIG. 2 can be replaced by a single midprocessor in the form of a DSP 42, as shown in FIG. 3. This DSP has at least two imaging modes, e.g., B mode and color flow imaging mode. In a first imaging mode, the DSP 42 receives first mode configuration data from the master controller 12 and first mode image data from beamformer 2. The DSP 42 processes the first mode image data in accordance with the first mode configuration data. In a second imaging mode, the DSP 42 receives second mode configuration data from the master controller 12 and second mode image data from beamformer 2. The DSP 42 processes the second mode image data in accordance with the second mode configuration data. For each mode, the processed data is output to the scan converter 6 for scan conversion. The scan-converted data is then sent to the display monitor 22 for each respective mode. For example, to duplicate the known modes employed in existing ultrasound imaging systems, the digital signal processor can be programmed to process image data from the beamformer 2 in any one of the following modes: B mode, M mode, color flow imaging mode and Doppler imaging mode.

Figure 5:
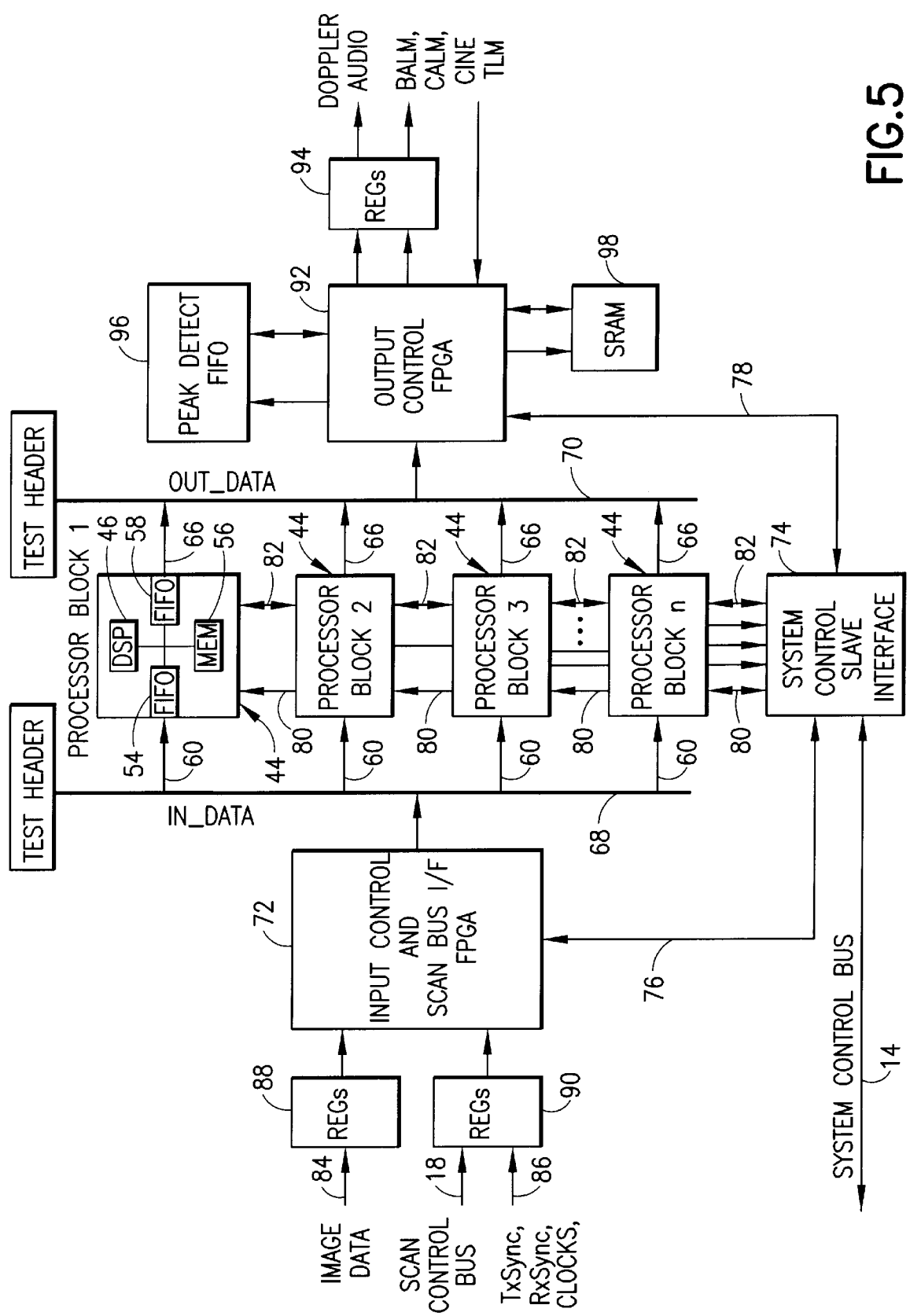
FIG. 5 is a block diagram showing the hardware architecture in accordance with a first preferred embodiment of the invention.

In accordance with the preferred embodiment of the invention, digital signal processing is performed by a plurality (e.g., n) of DSP blocks 44 arranged in parallel, as shown in FIG. 5. Each processor block comprises a DSP 46. The processor blocks 44 are designed with large buffer memories to allow double buffering of the image and configuration data for all modes concurrently. This double buffering of the data allows processing to occur on one data set while another is being collected.

In accordance with one preferred embodiment, the vector data derived from a single beam 100 (see FIG. 4) transmitted into a body 102 by a transducer 20 can be partitioned into overlapping segments. These segments are then processed by respective DSPs of the DSP block array. The addition of more DSP blocks, in a data-segmented parallel architecture, can provide more time for each DSP to complete its tasks. The time increase is limited by the resulting segment size and size of segment overlap required for specific DSP functions. Functions like filters typically have multi-pixel kernels which create the overlap requirement. In the case where multiple transmit focal zones are used, the high-focus portions of the respective beams are spliced together (as described below) to form a vector which is then partitioned into overlapping segments for processing by multiple DSPs.

Figure 4:
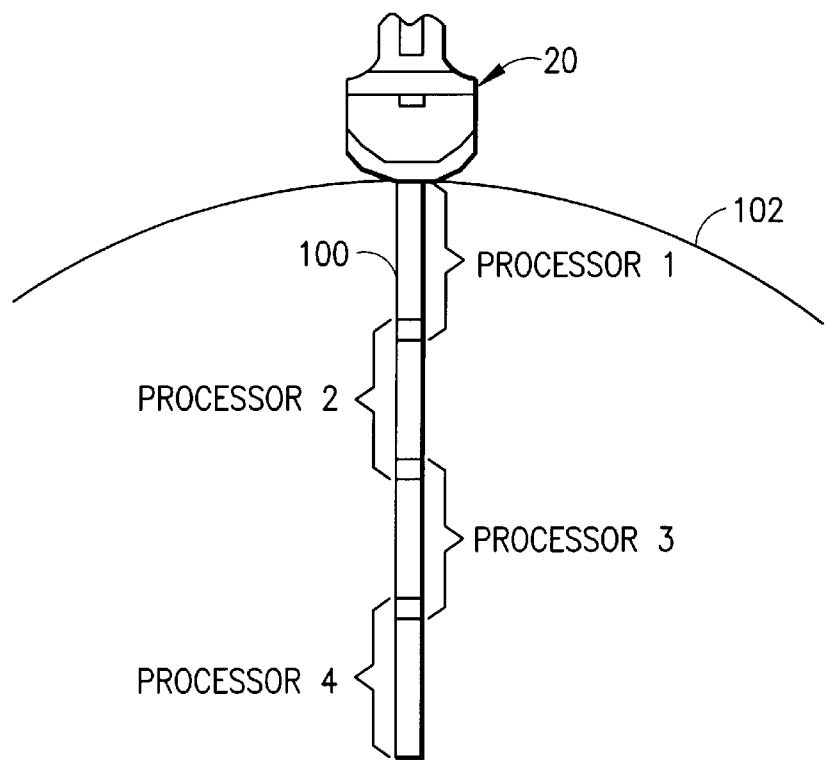
FIG. 4 is a schematic illustrating the segmentation of image data amongst a plurality of DSP blocks in accordance with the preferred embodiments of the invention.

The DSP image data segmentation can be made either down range (as shown in FIG. 4) or across vector spatial locations (not shown). In one example of the latter type of image data segmentation, vectors acquired from respective transmit beams directed at different angles can be parsed amongst different DSPs, one vector per processor. At any one given time, all modes (color flow, B, Doppler and M) must be processed using the same split format across the DSP blocks. When configured to split the processing across vectors, the position numbers must sequence identically for all of the firings or splices within a given interleave or confocal group. When configured to split down range, an overlap of image data between DSP blocks is required. Small overlap sections of the image data are sent to two DSP blocks. The overlap region of each segment needs to be long enough for filters to be filled and emptied. For FIR filters set at the center, an overlap equal to the number of filter taps is required. Across-vector segmentation limits filtering across vectors.

Alternatively, the system can alternate amongst the various modes, e.g., by sending one vector to a first DSP block programmed to process the signal according to a first imaging mode and sending the next receive beam to a second DSP block programmed to process the signal according to a second imaging mode. Receive vectors derived from successive transmit beams having the same transmit focal zone and the same transmit characteristics can be processed in accordance with different modes by different DSPs. It will be appreciated that the angle of the transmit beams could be varied while at the same time changing the receive beam processing mode in the DSPs.

In addition to the parallel DSP architecture to support data segmentation, some measure of pipelining could be used. This would use a mix of 2 to 4 DSPs in parallel to segment vectors down range and perhaps two deep in series behind these to provide a pipeline. The pipeline through buffering would allow sharing of the processing (math instructions) between piped DSPs while the time available for processing remained constant, so each piped DSP would have fewer instructions to execute in the same amount of time. Similar to parallel data segmentation, pipelining allows more time to process the data. It also can provide an architecture more friendly for hardware design.

Figure 6:
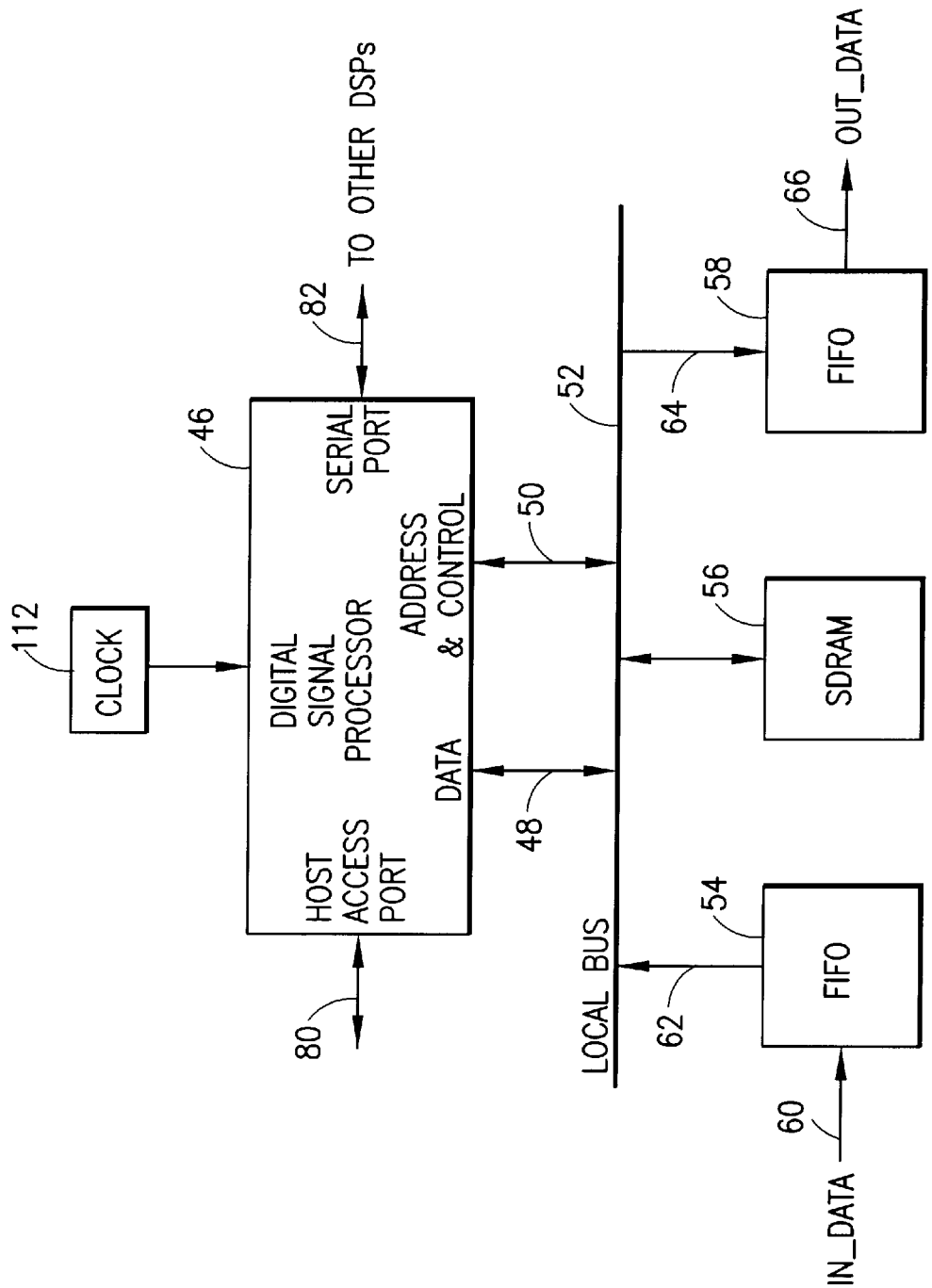
FIG. 6 is a block diagram showing the architecture of a DSP block in accordance with the first preferred embodiment of the invention.

As better seen in FIG. 6, each processor block comprises a DSP 46 connected via data lines 48 and address and control lines 50 to a local bus 52. The processor block also comprises an input FIFO 54, an SDRAM 56 and an output FIFO 58, each communicating with the DSP 46 via the local bus 52. The local bus 52 is used to move image data out of the input FIFO 54 and into a temporary internal (to the DSP) SRAM buffer, moving the data out of the internal SRAM buffer and into the SDRAM 56, moving image data from the DSP 46 into the output FIFO 58 after processing, SDRAM refreshes, moving image data into and out of the DSP from SDRAM for processing and perhaps for code fetching if all of the code does not fit within the processor's internal memory. This bus activity can run concurrently with the internal processing, unless the DSP is waiting for data or code, by using a direct memory access (DMA) capability built into the DSP.

Image data received by input FIFO 54 on data lines 60 is stored temporarily in FIFO 54 before being sent to the DSP 46 via data lines 62, local bus 52 and data lines 48. The image data is then processed by the DSP 46.

During signal processing, image data is moved into and out of the SDRAM 56. As seen in FIG. 6, each DSP block lacks a corner turner memory for color flow signal processing. Instead the SDRAM 56 is used for rotating the color flow data vector arrangement. Vectors are written down range. Some functions like the wall and flow estimations process this data at each depth, across multiple vectors within a firing packet, to make the estimates. Vector data arranged in the SDRAM 56 within row(s) can be accessed much faster than data arranged across columns. The SDRAM 56 is double banked to allow processing of the old data while new data is received. The memory size is driven by the maximum vector sample depth, number of pipes, packet size, interleave factor and the data width. The packet size refers to the number of vectors from the same spatial location that are to be used in a particular flow calculation. This is also referred to as the firing group. The interleave factor refers to the number of different vector spatial locations that are to be stored concurrently.

After signal processing, the image data is sent from the DSP 46 to the output FIFO 58 via data lines 48, local bus 52 and data lines 64. Processed image data received by output FIFO 58 on data lines 64 is stored temporarily in FIFO 58 before being output on data lines 66, the ultimate destination of this output image data being the scan converter.

Returning to FIG. 5, the data lines 60 into the input FIFOs 54 for all DSP blocks 44 are connected to an input data bus 68. Similarly, the data lines 66 out of the output FIFOs 58 for all DSP blocks 44 are connected to an output data bus 70. The DSP blocks 44 are connected in parallel between the input and output data buses. The circuit board shown in FIG. 5 has interfaces for the image input data from the equalization board and the scan control bus configuration data (input control and scan bus interface 72), the system control bus configuration data (system control slave interface 74), and the scan converter image output data (output controller 92). The input and output controllers 72 and 92 are preferably field-programmable gate arrays (FPGAs). The number of active DSP blocks on the board is configurable by the system control slave interface 74.

The image input data on line 84 from the equalization board is input to block 72 via registers 88. The scan control bus 18 for carrying scan control bus configuration data is connected to block 72 via registers 90. Synchronization signals TxSync and RxSync and clock signals provided on line 86 control the flow of scan control bus configuration data through the registers 90 to block 72.

System control bus configuration data for midprocessor functionality major mode changes is provided by the master controller to a system control slave interface 74 via the system control bus 14. The system control slave interface 74 provides this configuration information to the DSP blocks 44 via a host port interface 80 which connects to a respective host access port on each DSP 46 (see FIG. 6). These transmissions of system control bus configuration data occur when imaging has stopped. The system control slave interface 74 preferably has the ability to reset and communicate with each DSP block 44 separately or as a whole. In addition, the DSPs in each block 44 and the system control slave interface 74 are connected in series via a serial interlink 82.

The input control and scan bus interface 72 provides the scan control bus configuration data to the DSPs on a vector rate. This higher-rate system configuration bus transmits vector tag data for the entire system after the start of each TxSync signal. Only a subset of the total scan control bus delivery is latched and used by the DSPs. This functionality is combined in the input control and scan bus interface 72 with the image data from line 84 as a header. The configuration data is delivered in advance of when it is to be used. This is followed by image data.

The configuration header is a fixed-length data set. Its data comes from the scan control bus and system control slave interface setup. The configuration header instructs the DSPs on the functions to be performed for the associated image data. The header is minimized were possible by providing pointers to arrays of setup data. All code and system control slave interface configuration data is resident within the DSP internal memory before image data arrives.

The image data from the equalization board is transferred to a common memory within each DSP block. The input logic 72 flags or interrupts the DSP blocks after data transfer is complete. It also tests for an error condition where the memory is full and data needs to be sent, and sends an interrupt signal to the system control slave interface 74 via lines 76. This provides a system scan sequence indicator. In addition to allowing the system control slave interface 74 to read a scan control bus and an image data sample, block 72 allows slave interface 74 to write data individually to the DSP block FIFOs.

The present invention uses a single array of off-the-shelf general-purpose DSP chips populated on one circuit board to implement all three major midprocessor functions; color flow imaging mode, B/M mode and spectral Doppler imaging mode. Design flexibility is greatly increased by capturing the DSP functionality in software, while the hardware is more generic and highly utilized. The configuration data for programming the DSPs to process in accordance with an operator-selected imaging mode is supplied by the master controller (12 in FIG. 1) to the DSP host access ports via the system control bus 14, system control slave interface 74 and host port interface 80. This design will facilitate the implementation of future changes without hardware redesign. Software-based field upgrades are of lower cost. This design is also highly scaleable.

The unified midprocessor hardware design of the invention alternates between the processing of color flow, Doppler, B-mode and M-mode data as it arrives from the equalization board. When programmed in the B/M mode, the DSPs determine the intensity of the echo signals returned from ultrasound scatterers; when programmed in the color flow imaging mode, the DSPs estimate the velocity of moving ultrasound scatterers; and when programmed in the Doppler imaging mode, the DSPs output spectra for gray-scale display as well as digital signals which are later converted into audio.

In both B-mode and color flow imaging mode processing, a splicing function is used to piece together sections of data from incoming vectors. During multi-transmit focal zone imaging the input control and scan bus interface 72 extracts the segments of higher focus which surround the transmit focal depth. These higher-focus vector segments are then concatenated (i.e., butt spliced) into a single output vector by the DSPs. The DSPs are also programmed to perform low-pass filtering to smooth the transition regions. Before any vectors arrive, the splicing function in input control and scan bus interface 72 is initialized by system control slave interface 74 via lines 76. The slave interface 74 loads the start and stop range depths which define the splice regions. The scan control bus 18 provides three vector tags used in splicing via registers 90. All of the vectors that are to be combined into one output vector are referred to as a packet. Interleave (color flow) or confocal (B mode) group refers to the vectors from different spatial positions that are to be concurrently spliced.

The input control and scan bus interface 72 gathers, windows, decimates, averages, segments and sends scan bus configuration and image data to the DSP blocks. The segmentation of this data across the DSP nodes is configured by the system control slave interface 74 via line 76 and is optionally also directed by the scan control bus tags. Depending on the segmentation of data across splice zones, two or more packets of splice zone data, each with its own header, may be written to any one DSP. The system control slave interface 74 can configure block 72 to hold a single sample of data to provide host diagnostic access.

The scan bus configuration data becomes headers for all of the data packets input to the DSP blocks. Windowing allows the input control logic to select a subsegment of a slave interface-defined portion of each vector. The unused beginning and ending regions of data are discarded. The I and Q data pipes are processed separately and identically. Before any vectors arrive, the system control slave interface 74 configures block 72.

In accordance with the preferred embodiment shown in FIG. 5, an output control FPGA 92 serves as an interface between the DSPs and the scan converter (6 in FIG. 1). The output controller 92 gathers configuration and image data to be sent to the scan converter. The configuration data will be delivered by the system control slave interface 74 via lines 78 and as headers on the image data from the DSP blocks. The image data can include B and M mode, color flow and Doppler types. M mode data can optionally be peak accumulated in peak detect FIFO 96. An SRAM 98 is used for staging the configuration and image data to be sent to the scan converter. The Doppler audio signals and the image data destined for the display memories are transmitted to the scan converter via registers 94.

The system control slave interface 74 sets up output controller 92 as it did the input controller 72. The input controller needed to know how to parse input data between the DSP blocks and the output controller needs to know how to combine output data from the DSP blocks. The instructions for combining data are provided by the system control slave interface and/or image data headers. After a vector of image data is completed, the vector is sent to the appropriate memory in the scan converter: M mode and Doppler data go to the timeline memory 40 (TLM), B mode data goes to the B-mode acoustic line memory 34 (BALM) and color flow data goes to the color acoustic line memory 32 (CALM). The cine memory (not shown in FIG. 2) can transparently gather image frames of color flow and B-mode data.

The output controller 92 contains the scan converter output logic. It repacks the segmented image data and delivers it to the scan converter. The system control slave interface 74 and the DSP image data headers configure block 92. Some of the interface configuration data goes into the B-mode and color flow output headers.

In accordance with the preferred embodiment, all code and configuration data is loaded from the host computer (i.e., master controller 12 in FIG. 1) through the system control slave interface 74 via the host port interface 80 (see FIG. 5). After reset, a DSP 46 will remain idle until it is started by a DSP slave interface interrupt. The code will be loaded into both external SDRAM and internal SRAM. The input controller 72 will provide an interrupt when a complete vector segment is in the input FIFO 54 ready to be read. Likewise the DSP 46 supplies an interrupt signal to the output controller 92 indicating that a complete vector segment is available to be read out from the output FIFO 58. This will require that one or more configuration values be supplied to each DSP for each mode. This value may be sent as a part of the DSP configuration, the input controller configuration (and then by header to the DSP), or calculated on the fly by the input controller.

A DSP of the type having a serial port may be used, as seen in FIG. 6. optionally, these serial ports are connected between DSP blocks for use as an inter-processor communication link 82. The DSP host access port is used to download all applications code from the host computer (master controller) through the system control slave interface 74. The applications code will be loaded into both the DSP external SDRAM and internal SRAM. The applications code and configuration memory are needed in all of the DSP blocks, but the image data is split across the DSP blocks.

The main task of the applications code is to provide signal processing of image data before scan conversion and display. Each of the ultrasound modes require unique signal processing, as previously described. The DSP applications software design will utilize a static load sharing mechanism initiated by a control platform. Once a mode's processing is initiated by the DSP control platform, it will process that data until complete. Preemption of this processing will be limited to the next vector. The control platform will provide the mechanism to initiate each mode's processing. When a mode's complete data set has been processed, the control platform then decides and initiates the next mode's data processing if appropriate.

Figure 7:
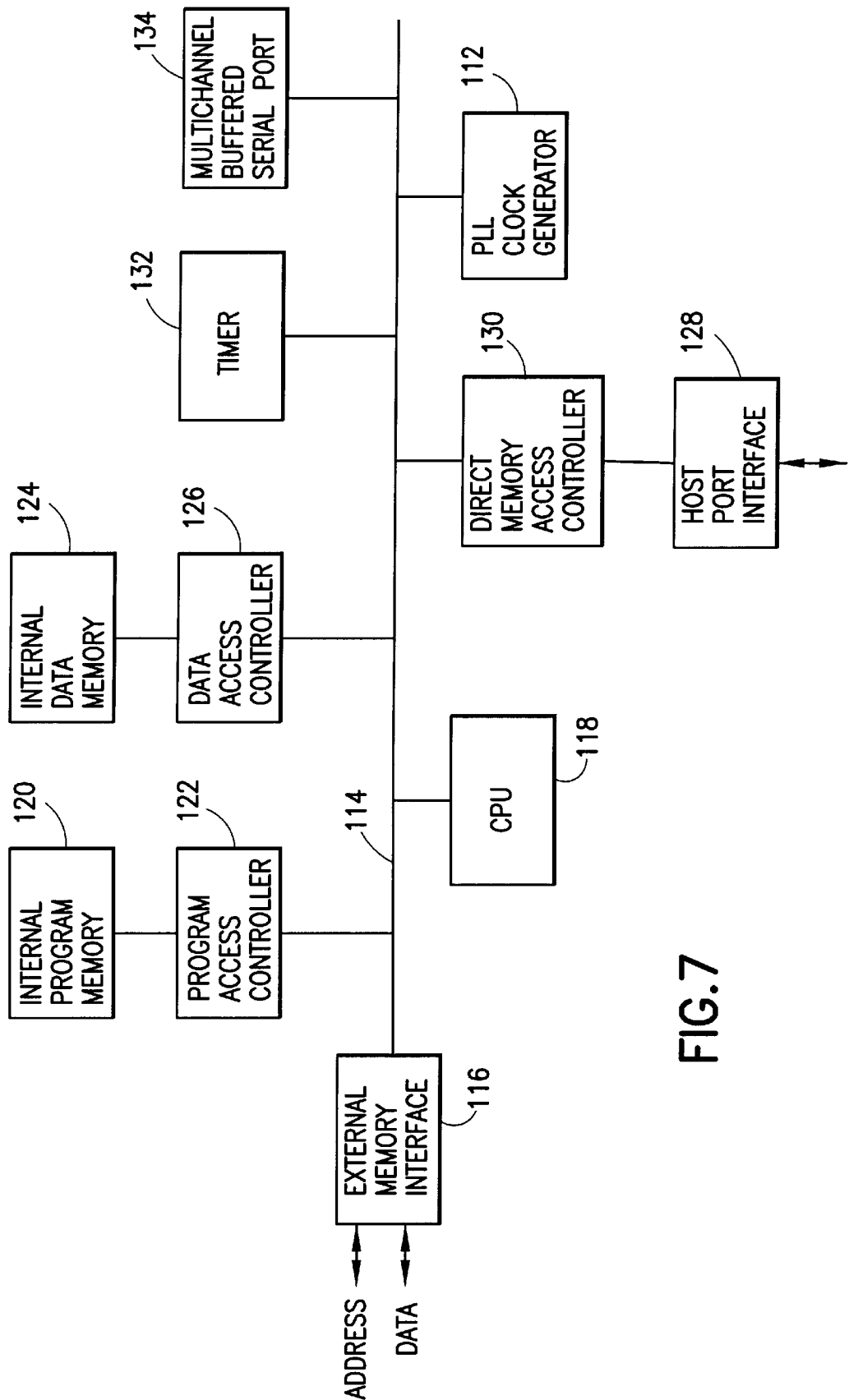
FIG. 7 is a block diagram showing the internal architecture of a DSP chip suitable for use in the preferred embodiments of the invention.

A commercially available DSP suitable for use in the invention is the TMS320C6201 manufactured by Texas Instruments, the main internal components of which are generally depicted in FIG. 7. This DSP comprises program/data buses 114 which communicate with the FIFOs 54 and 58 and the SDRAM 56 shown in FIG. 6 via an external memory interface 116. Applications code is stored in internal program memory 120; image data and headers are stored in internal data memory 124. The internal program memory 120 communicates with the program bus of buses 114 via a program access controller 122; the internal data memory 124 communicates with the data bus of buses 114 via a data access controller 126. The bus activity between the DSP and the FIFOs and SDRAM in the DSP block can run concurrently with the DSP internal processing, unless the DSP is waiting for data or code, via a host port interface 128 and a direct memory access (DMA) controller 130. In particular, acquired vector data from one firing can be loaded into the internal data memory 124 of the DSP while acquired vestor data from an earlier firing is being processed inside the CPU 118. As seen in FIG. 7, the TMS320C6201 also incorporates a PLL clock generator 112, a timer 132 and at least one multichannel buffered serial ports 134, all connected to the buses 114.

Figure 8:
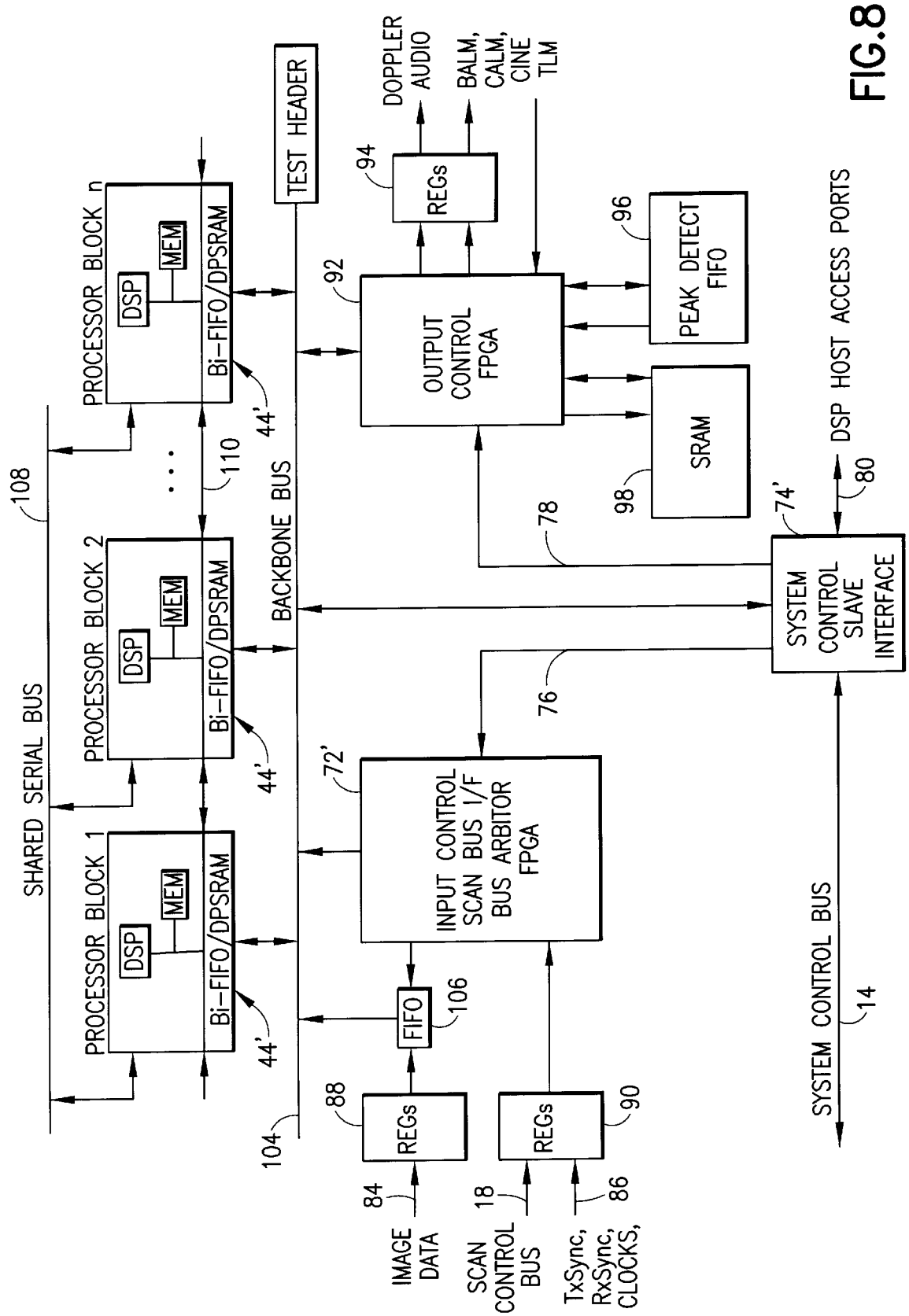
FIG. 8 is a block diagram showing the hardware architecture in accordance with a second preferred embodiment of the invention.

An alternative architecture for a multi-DSP midprocessing section of an ultrasound imaging system is depicted in FIG. 8. A multiplicity of processor blocks 44' are connected to a bidirectional backbone bus 104. Each block 44' comprises a DSP, a random access memory and a bidirectional FIFO (or a dual-port static RAM). Image data is input to the DSP blocks 44' via registers 88, FIFO 106 and backbone bus 104. Since the flow of information on the backbone bus 104 is bidirectional, the input controller 72' also acts as a bus arbiter by holding image data in the FIFO 106 to avoid contention on the backbone bus. In this preferred embodiment, the system control slave interface 74' communicates with the backbone bus. The DSP block 44' can communicate with each other either via a shared serial bus 108 which connects the serial ports on the DSP chips or via serial interprocessor communication lines 110. The elements in FIG. 8 which bear the same reference numerals as corresponding elements shown in FIG. 5 have the same functionality as previously described with reference to FIG. 5 and that description is not repeated here for the sake of economy.

The foregoing preferred embodiments have been disclosed for the purpose of illustration. Variations and modifications of the concept of the invention will be readily apparent to persons skilled in the art. For example, it should be appreciated that the invention can be employed in either RF or baseband systems. In RF systems, the RF signals are summed, equalized and envelope detected without intervening demodulation to baseband. All such variations and modifications are intended to be encompassed by the claims set forth hereinafter.

I claim:

1. An ultrasound imaging system comprising:

an ultrasound transducer array comprising a multiplicity of transducer elements;

a transmit beamformer for pulsing selected transducer elements during a series of transmit firings;

a receive beamformer coupled to selected transducer elements of said transducer array for acquiring a respective receive signal subsequent to each transmit firing;

a first signal processor programmable in a first imaging mode to process first receive signals into a first image signal having a first image format in accordance with a first application code and programmable in a second imaging mode to process second receive signals into a second image signal having a second image format in accordance with a second application code, wherein said first signal processor can operate in accordance with only one of said first and second application codes at any given time; and a display device for displaying an image having an image portion which is a function of said first image signal in said first imaging mode and of said second image signal in said second imaging mode.

2. The ultrasound imaging system as recited in claim 1, further comprising:

an operator interface for selecting one of said first and second imaging modes; and a system controller for providing said first application code in response to selection of said first imaging mode and said second application code in response to selection of said second imaging mode.

3. The ultrasound imaging system as recited in claim 2, wherein said first signal processor comprises memory for storing said first application code in said first imaging mode and said second application code in said second imaging mode.

4. The ultrasound imaging system as recited in claim 1, wherein said first and second imaging modes are selected from a group consisting of B mode, M mode, color flow imaging mode and Doppler imaging mode.

5. The ultrasound imaging system as recited in claim 1, wherein in said first imaging mode said first signal processor comprises means for envelope detection.

6. The ultrasound imaging system as recited in claim 1, wherein in said first imaging mode said first signal processor comprises means for velocity estimation.

7. The ultrasound imaging system as recited in claim 1, wherein in said first imaging mode said first signal processor comprises means for fast Fourier transformation.

8. The ultrasound imaging system as recited in claim 2, further comprising a second signal processor and an input controller for partitioning first and second segments of said receive signals among said first and second signal processors respectively, wherein said first and second signal processors process said first and second segments of said receive signals into first and second segments respectively of said first image signal in said first imaging mode, and into first and second segments respectively of said second image signal in said second imaging mode.

9. The ultrasound imaging system as recited in claim 8, further comprising an output controller for combining said first and second segments to form said first image signal in said first imaging mode and said second image signal in said second imaging mode.

10. The ultrasound imaging system as recited in claim 8, wherein said first and second segments of said receive signals are derived from first and second ranges respectively of a receive beam.

11. The ultrasound imaging system as recited in claim 10, wherein said first and second ranges of said receive beam are overlapping.

12. The ultrasound imaging system as recited in claim 8, wherein said first and second segments of said receive signals are derived from first and second receive beams having different beam angles.

13. The ultrasound imaging system as recited in claim 2, further comprising a second signal processor and an input controller for partitioning first and second segments of said receive signals among said first and second signal processors respectively, wherein said first and second segments of said receive signals are derived from first and second receive beams having the same or different beam angles, said first signal processor is programmed to process said first segment of said receive signals into a segment of a first image signal having said first image format, and said second signal processor is programmed to process said second segment of said receive signals into a segment of a second image signal having said second image format.

14. The ultrasound imaging system as recited in claim 9, further comprising a slave interface connected to said first and second signal processors, to said input controller and to said output controller, wherein in said first and second imaging modes said system controller sends first and second configuration data respectively via said slave interface to said first and second signal processors, to said input controller and to said output controller.

15. The ultrasound imaging system as recited in claim 14, wherein said first signal processor is a digital signal processor chip comprising a central processing unit, an internal memory, an external memory interface, and a direct memory access controller, all connected to a local bus, and a host port interface for coupling said direct memory access controller to said slave interface, wherein said direct memory access controller is configured via said host port interface to move receive signals from one firing from said external memory interface to said internal memory while receive signals from an earlier transmit firing are being processed inside said central processing unit.

16. A method for configuring an ultrasound imaging system having a programmable signal processor and an operator interface, comprising the steps of:

storing first and second application codes comprising instructions for programming said signal processor to process signals in accordance with first and second imaging modes respectively;

operating said operator interface to select one of said first and second imaging modes; and programming said signal processor with one of said first and second application codes corresponding to said selected one of said first and second imaging modes in response to said operating step.

17. The method as recited in claim 16, further comprising the step of configuring said signal processor in accordance with said one of said first and second application codes corresponding to said selected one of said first and second imaging modes.

18. The method as recited in claim 16, wherein said first and second imaging modes are selected from a group consisting of the B mode, M mode, color flow imaging mode and Doppler imaging mode.

19. A system for imaging ultrasound scatterers comprising:

means for transmitting ultrasound waves toward said ultrasound scatterers;

means for acquiring echo signals derived from ultrasound waves returned from said ultrasound scatterers;

an operator interface for selecting one of a plurality of imaging modes;

a programmable signal processor for processing said echo signals into an image signal having an image format determined by said selected imaging mode;

a system controller for providing a predetermined application code corresponding to said selected imaging mode for programming said programmable signal processor in response to selection of said selected imaging mode via said operator interface; and a display device for displaying an image having an image portion which is a function of said image signal.

20. A method for operating an ultrasound imaging system having a transducer array, an operator interface and a programmable signal processor, comprising the steps of:

operating said operator interface to select one of a plurality of imaging modes;

programming said signal processor with an application code determined by said selected imaging mode in response to selection of said selected imaging mode via said operator interface;

transmitting ultrasound waves from said transducer array toward said ultrasound scatterers;

acquiring echo signals derived from ultrasound waves returned from said ultrasound scatterers and detected by said transducer array;

inputting said echo signals into said programmed signal processor for processing said echo signals in accordance with said application code to form an image signal; and displaying an image having an image portion which is a function of said image signal.

21. An ultrasound imaging system comprising:

an ultrasonic transducer array;

means for transmitting ultrasound waves from said transducer array toward said ultrasound scatterers;

means for acquiring echo signals derived from ultrasound waves returned from said ultrasound scatterers and detected by said transducer array;

an operator interface for selecting one of a plurality of imaging modes;

a programmable signal processor;

means for programming said signal processor with an application code determined by said selected imaging mode in response to selection of said selected imaging mode via said operator interface;

means for inputting said echo signals into said programmed signal processor for processing said echo signals in accordance with said application code to form an image signal; and a display device for displaying an image having an image portion which is a function of said image signal.

22. An ultrasound imaging system comprising:

an ultrasound transducer array comprising a multiplicity of transducer elements;

a transmit beamformer for pulsing selected transducer elements during a series of transmit firings;

a receive beamformer coupled to selected transducer elements of said transducer array for acquiring a respective vector of receive data subsequent to each transmit firing;

a plurality of signal processors programmed to process receive data into image data in accordance with an imaging mode;

an input controller for partitioning a plurality of segments of a vector of receive data among said plurality of signal processors, wherein each signal processor processes a respective receive data vector segment to form a respective image data vector segment;

an output controller for combining said image data vector segments to form a vector of image data; and a display device for displaying an image having an image portion which is a function of said image data vector.

23. The ultrasound imaging system as recited in claim 22, wherein said imaging mode is selected from a group consisting of B mode, M mode, color flow imaging mode and Doppler imaging mode.

24. The ultrasound imaging system as recited in claim 22, further comprising:

an operator interface for selecting said imaging mode from a plurality of imaging modes; and a system controller for providing an application code in response to selection of said imaging mode, wherein said signal processors are programmed in accordance with said application code in said imaging mode.

25. A system for imaging ultrasound scatterers, comprising:

an ultrasound transducer array comprising a multiplicity of transducer elements;

a transmit beamformer for pulsing selected transducer elements during a series of transmit firings;

a receive beamformer coupled to selected transducer elements of said transducer array for acquiring a respective receive signal subsequent to each transmit firing;

an operator interface for selecting one of a plurality of imaging modes;

a programmable signal processor for processing said receive signals into image signals having an image format determined by said selected imaging mode;

a display monitor for displaying an image having an image portion which is a function of said image signal; and a computer programmed to perform the following steps:
(a) detecting a change in the state of said operator interface indicating selection of one of a plurality of imaging modes;
(b) programming said signal processor with an application code determined by said selected imaging mode in response to said detecting step.

* * * * *